US00PP35124P2

(12) United States Plant Patent
Dirr et al.

(10) Patent No.: US PP35,124 P2
(45) Date of Patent: Apr. 25, 2023

(54) ***HYDRANGEA* PLANT NAMED 'CE-01-20'**

(50) Latin Name: *Hydrangea macrophylla*
Varietal Denomination: CE-01-20

(71) Applicant: Premier Introductions, Inc., Watkinsville, GA (US)

(72) Inventors: Michael Dirr, Bogart, GA (US); Jeff Beasley, Lavonia, GA (US); Mark Griffin, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 17/894,344

(22) Filed: Aug. 24, 2022

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP17,660 P2 * 4/2007 Johnson, Jr. ..... A01H 5/02 Plt./250

* cited by examiner

*Primary Examiner* — June Hwu
(74) *Attorney, Agent, or Firm* — Cassandra Bright

(57) ABSTRACT

A new and distinct cultivar of *Hydrangea* plant named 'CE-01-20' is disclosed, characterized by bright yellow foliage in the spring, turning to yellow-green in the summer, pink mophead inflorescence in non-aluminum based media and blue inflorescence in aluminum based media, and compact, rounded to spreading growth habit. The new variety is a *Hydrangea*, typically produced as an outdoor ornamental plant.

3 Drawing Sheets

Figure 1:
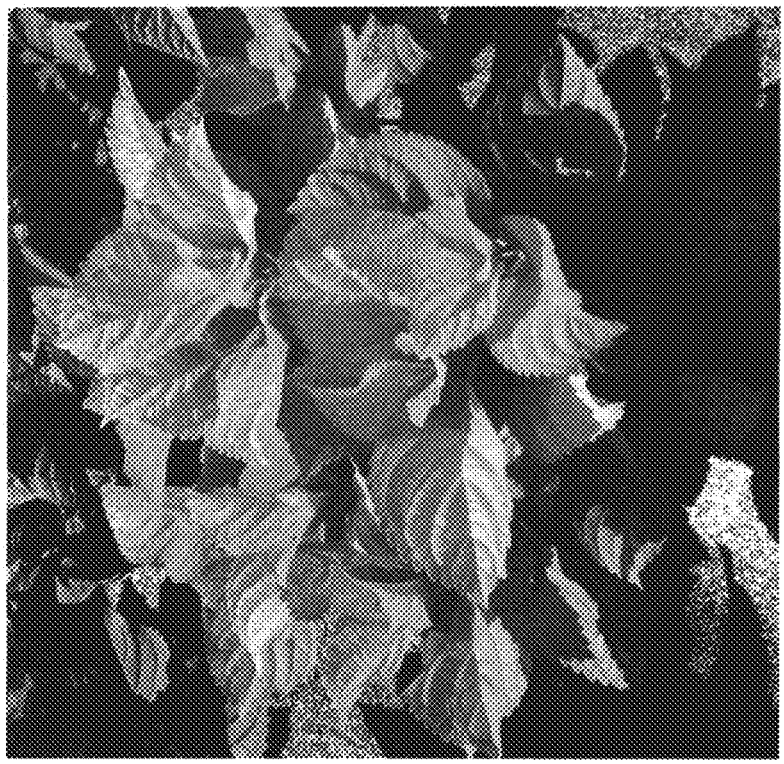

Latin name of the genus and species: *Hydrangea macrophylla.*

Variety denomination: 'CE-01-20'.

BACKGROUND OF THE INVENTION

The present invention relates to a new and distinct cultivar of *Hydrangea macrophylla*, a member of the Hydrangeaceae family, hereinafter referred to by its cultivar name 'CE-01-20'. This cultivar is grown primarily as an ornamental for landscape use and for use as a potted plant. The cultivar originated from an open pollination of *Hydrangea macrophylla* 'McKay', U.S. Plant Pat. No. 28,757, in Watkinsville, Ga., in 2020, and was selected from the progeny by continued evaluation for growth habit, floral, and foliage characteristics.

'CE-01-20' has been asexually reproduced by softwood cuttings since 2020 in Watkinsville, Ga. The characteristics of the cultivar have been stable and reproduced true to type in successive vegetative generations.

SUMMARY OF THE INVENTION

'CE-01-20' has not been observed under all possible environmental conditions. The phenotype may vary somewhat with changes in light, temperature, soil and rainfall without, however, any variance in genotype.

The following traits have been repeatedly observed and are determined to be the unique characteristics of 'CE-01-20.' These characteristics in combination distinguish 'CE-01-20' as a new and distinct *Hydrangea* cultivar:

1. Bright yellow foliage in the spring, turning to yellow-green in the summer.
2. Pink mophead inflorescence in non-aluminum-based media and blue inflorescence in aluminium-based media.
3. Compact, rounded to spreading growth habit.

PARENT COMPARISON

Plants of the new cultivar *Hydrangea* 'CE-01-20' can be compared to the seed parent variety in most horticultural characteristics, however, plants of 'CE-01-20' differ in the following:

1. 'CE-01-20' has bright yellow foliage in spring turning to yellow-green in the summer, whereas *Hydrangea macrophylla* 'McKay' has dark green foliage.
2. 'CE-01-20' is a mophead and 'McKay' is lacecap.

COMMERCIAL COMPARISON

Plants of the new cultivar *Hydrangea* 'CE-01-20' can be compared to the commercial variety *Hydrangea macrophylla* 'Lemon Daddy', U.S. Plant Pat. No. 17,660. Plants of 'CE-01-20' are similar to plants of 'Lemon Daddy' in most horticultural characteristics, however, plants of 'CE-01-20' differ in the following:

1. 'CE-01-20' holds its golden-yellow color turning to yellow-green throughout the growing season; whereas, the foliage on 'Lemon Daddy' turns green with heat as the season progresses.
2. 'Lemon Daddy' is a much larger shrub with weaker stems and slightly larger leaves than 'CE-01-20'.

Plants of the new cultivar *Hydrangea* 'CE-01-20' can be compared to the commercial variety *Hydrangea macrophylla* 'Yellowleaf', U.S. Plant Pat. No. 12,701. Plants of 'CE-01-20' are similar to plants of 'Yellowleaf' in most horticultural characteristics, however, plants of 'CE-01-20' differ in the following:

1. 'Yellowleaf' is very frost sensitive, whereas 'CE-01-20' has normal tolerance to frost.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea*.

FIG. 1: A two-year-old 'CE-01-20' plant foliage in the spring.

Figure 2:
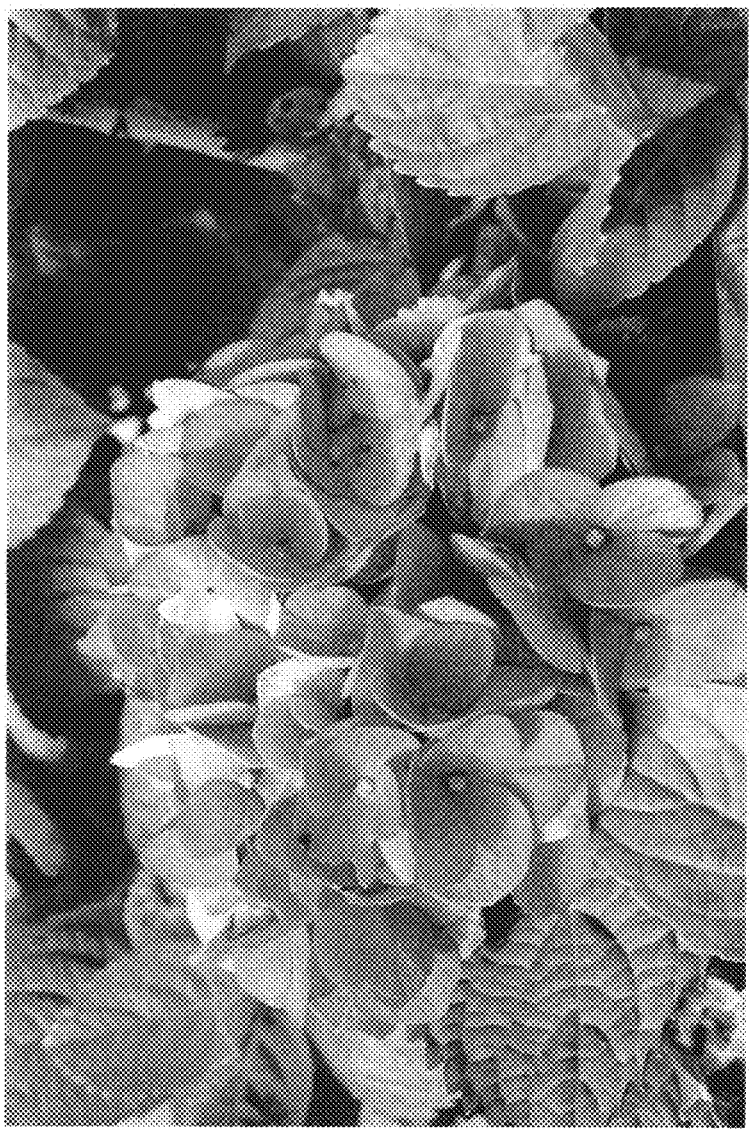

FIG. 2: A two-year-old 'CE-01-20' plant grown with aluminum.

Figure 3:
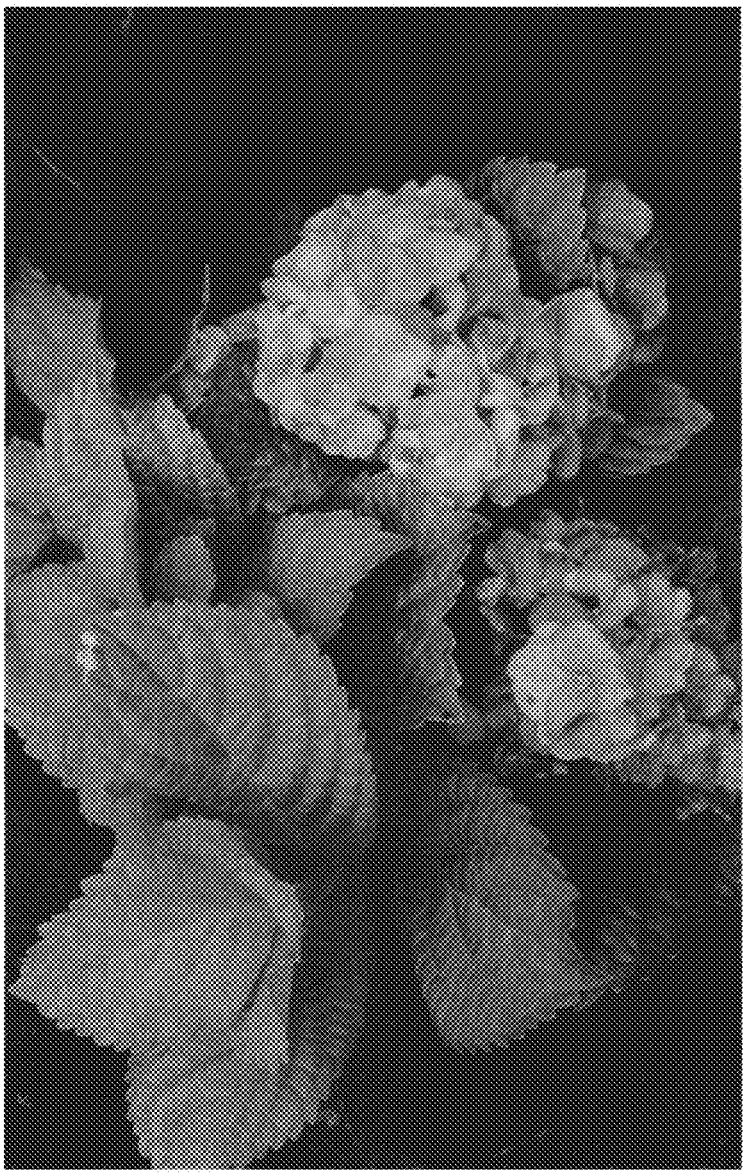

FIG. 3: A two-year old 'CE-01-20' plant grown without aluminum.

DETAILED BOTANICAL DESCRIPTION

In the following description, color references are made to The Royal Horticultural Society Colour Chart, 2015 Edition, except where general terms of ordinary dictionary significance are used. Plants used for the description were grown in 23.03 L containers under 50% shade under outdoor conditions in a nursery in Watkinsville, Ga. Plants were about two years old when the description was recorded. Two groups of plants were used for the description to describe the flower colors with and without aluminum. The first group was grown in a medium consisting of composted pine bark, with no aluminum present and a pH of 5.4. The second group was grown in a medium consisting of composted pine bark that was amended with 60 grams of aluminum sulphate and a pH of 5.3. Aluminum only affects flower including sepal, petal, pistil and stamen colors. Therefore, colors with and without aluminum are only specified for floral parts.

Botanical classification: *Hydrangea macrophylla* 'CE-01-20'.

PROPAGATION

Typical method: Vegetatively by stem cuttings.

Root initiation: Approximately 14 days at 32° C.

Time to produce rooted cutting: About 3 months at 32° C. during summer.

Time to produce a finished crop: In a 11.4 L container potted with a 0.041 L liner pot, about 9 months.

Roots: Root description: numerous, fine, fibrous and well-branched. Color: RHS White NN155A.

PLANT

Plant type: Rounded and spreading deciduous shrub.

Height: 50 cm.

Plant spread: 109 cm.

Age of plant described: Approximately 2 years.

Branching characteristics: Freely-branching. Pinching enhances branching.

*Number of lateral branches*.—About 8 per plant.

First year stems:

*Length*.—30 cm.

*Width*.—4 mm.

*Color*.—RHS Yellow-Green N144C.

*Shape*.—Round.

*Strength*.—Flexible.

*Texture*.—Smooth.

Second year stems:

*Length*.—45 cm.

*Width*.—6 mm.

*Color*.—RHS Brown 199B.

*Shape*.—Round.

*Strength*.—Easily broken.

*Texture*.—Woody. Exfoliation begins on second year and older stems, flaky and stringy, the color is RHS Yellow 161A.

Stem fasciation: Not present.

Stem lenticels: Only observed on new growth. Very sparse. Round, about 2 mm in diameter. Colored near Greyed-Purple 187A.

Vegetative buds:

*Arrangement*.—Opposite.

*Shape*.—Ovoid.

*Length*.—2 mm.

*Width*.—1 mm.

*Color*.—RHS Yellow-Green N144B.

FOLIAGE

Leaf:

*Arrangement*.—Opposite, simple.

*Shape*.—Ovate.

*Length*.—15 cm.

*Width*.—12 cm.

*Apex*.—Acuminate.

*Base*.—Cuneate.

*Margin*.—Serrate.

*Texture of top surface*.—Glabrous.

*Texture of bottom surface*.—Glaucescent.

*Color*.—Young foliage upper side: RHS Yellow-Green N144A. Young foliage under side: RHS Yellow-Green N144A. Mature foliage upper side: RHS Yellow-Green 153D. Mature foliage, under side: RHS Yellow-Green 153D. Summer foliage upper side: RHS Yellow-Green 144A. Summer foliage, under side: RHS Yellow-Green 147C. Fall foliage upper side: RHS Red-Purple N77A mixed with Yellow-Green 144A. Fall foliage, under side: RHS Red-Purple N77A mixed with Yellow-Green 144A.

Venation:

*Type*.—Pinnate.

*Color*.—Young, upper side: RHS Yellow-Green 144B. Young, under side: RHS Yellow-Green 145C. Mature, upper side: RHS Yellow-Green 145C. Mature, under side: RHS Yellow-Green 145C.

Petiole:

*Length*.—1.3 cm.

*Width*.—5 mm.

*Color*.—Upper side: RHS Yellow-Green 145A. Under side: RHS Yellow-Green 145A.

*Texture*.—Smooth, glabrous. Petiole is grooved on upper side, and crescent-shaped in cross section.

INFLORESCENCE

Natural flowering season: Early to mid-summer. The inflorescence is effective for about 8 weeks.

Inflorescence type: Mophead.
*Height*.—5 cm.
*Diameter*.—10 cm.
Fragrance: None.
Bud:
*Bud length*.—6 mm.
*Bud diameter*.—4 mm.
*Bud shape*.—Round.
*Bud color*.—Prior to opening: RHS Yellow-Green 145C. When opening, with aluminum: RHS Purplish Blue 100A. When opening, without aluminum: RHS Purplish Pink N66D.
Sterile florets:
*Flowers per inflorescence*.—About 275.
*Shape*.—Ovoid.
*Tip*.—Obtuse.
*Base*.—Acute.
*Margin*.—Entire.
*Diameter*.—3 cm.
*Length*.—About 3.2 cm.
Sepals:
*Number per flower*.—4.
*Length*.—2 cm.
*Width*.—1.5 cm.
*Shape*.—Broad, rounded deltate.
*Margin*.—Entire, infrequently crenulate.
*Attitude*.—Semi-erect.
*Undulation*.—Absent.
*Apex*.—Broad, rounded.
*Base*.—Truncate.
*Overlap*.—Less mature florets have strong overlapping sepals, mature florets medium overlapping sepals.
*Texture*.—Upper side: Smooth. Under side: Smooth.
*Color*.—At maturity, with aluminum: Upper side: RHS Blue 101C. Under side: RHS Purplish Blue 97B. At maturity, without aluminum: Upper side: RHS Purplish Pink 73A. Under side: RHS Purplish Pink 73B. Aged sepals, with aluminum: Upper side: RHS Light Purple 85C. Under side: RHS Light Purple 85D. Aged sepals, without aluminum: Upper side: RHS White 155B with a hint of Purplish Pink 62D. Under side: RHS White I55C with a hint of Purplish Pink 62D.
Fertile flowers:
*Flowers per inflorescence*.—About 55.
*Size*.—About 4 mm in diameter.
*Conspicuousness*.—Inconspicuous.
Petals:
*Number per flower*.—5.
*Shape*.—Ovate.
*Tip*.—Acuminate.
*Base*.—Truncate.
*Margin*.—Entire.
*Length*.—3 mm.
*Width*.—1.5 mm.
*Texture*.—Smooth, no pubescence.
*Color*.—With aluminum, upper side: RHS Purplish Blue 100B. With aluminum, under side: RHS Purplish Blue 100C. Without aluminum, upper side: RHS Purplish Pink 63C. Without aluminum, under side: RHS Purplish Pink 62D.
Peduncle:
*Length*.—5.5 cm.
*Diameter*.—4 mm.
*Angle*.—Upright.
*Strength*.—Moderately strong and flexible.
*Color*.—RHS Yellow-Green 144C.
Pedicel:
*Length*.—1.2 cm.
*Diameter*.—1 mm.
*Angle*.—45°.
*Strength*.—Moderately strong and flexible.
*Texture*.—Smooth.
*Color*.—RHS Purplish Pink N66D.

REPRODUCTIVE ORGANS

Stamens:
*Number*.—4 to 5 per flower.
*Filament length*.—3 mm.
*Filament color*.—With aluminum: RHS Purplish Blue 100B. Without aluminum: RHS Yellow-Green 157C.
Anthers:
*Length*.—About 1 mm.
*Width*.—0.5 mm.
*Color*.—With aluminum: RHS Purplish Blue 100B. Without aluminum: RHS Yellow-Green 157A.
*Pollen amount*.—Moderate.
*Pollen color*.—RHS Yellow-White 155D.
Pistil:
*Number*.—1.
*Length*.—3 mm.
*Width*.—1.5 mm.
*Color*.—With aluminum: RHS Purplish Blue 100B. Without aluminum: RHS Yellow-Green 155A.
Stigma:
*Number*.—2 or 3.
*Shape*.—Round.
*Color*.—RHS Green-White 157D.
*Style length*.—2 mm.
*Style color*.—With aluminum: RHS Purplish Blue 100B. Without aluminum: RHS Yellow-Green 155A.

OTHER CHARACTERISTICS

Fruit:
*Number*.—Varies widely.
*Shape*.—Spatulate.
*Length*.—3 mm.
*Width*.—2 mm.
*Color*.—During ripening: RHS Purplish Pink 54B. At maturity: Near RHS Brown 200C.
Seeds:
*Number*.—About 50 seeds per capsule.
*Shape*.—Round.
*Length*.—0.5 mm.
*Width*.—0.5 mm.
*Color*.—Near RHS Brown 199C.
Disease resistance: Susceptibility or resistance to diseases beyond that typically found in other *Hydrangea macrophylla* plants has not been observed.
Drought tolerance and cold tolerance: USDA Hardiness Zone Map (2012): Zones 7-9.

What is claimed is:

1. A new and distinct cultivar of *Hydrangea* plant named 'CE-01-20' as herein illustrated and described.

* * * * *